United States Patent

Cook et al.

[11] 4,052,160
[45] Oct. 4, 1977

[54] CORROSION INHIBITORS

[75] Inventors: Barry Cook, Manchester; John Grey Dingwall, Sale; Brian Martin Thomas, Stockport, all of England

[73] Assignee: Ciba-Geigy Corporation, New York, N.Y.

[21] Appl. No.: 707,127

[22] Filed: July 20, 1976

[30] Foreign Application Priority Data

July 23, 1975 United Kingdom ............. 30719/75
Apr. 13, 1976 United Kingdom ............. 14966/76

[51] Int. Cl.² .......................................... C23F 11/16
[52] U.S. Cl. .................................. 21/2.7 A; 106/14;
21/2.5 A; 252/8.55 E; 252/180; 252/389 A
[58] Field of Search ............ 252/389 A, 180, 181, 252/86, 87, 8.55 E; 21/2.5 A, 2.7 A; 260/502.4 R, 502.4 P

[56] References Cited

U.S. PATENT DOCUMENTS 3,619,427  11/1971  Kautsky ......................... 21/2.7 A

FOREIGN PATENT DOCUMENTS 2,115,427  10/1971  Germany ........................ 252/389 A
2,310,450   9/1974  Germany ........................ 252/389 A
2,441,096  11/1975  Germany ........................ 252/389 A
2,505,435   8/1976  Germany ........................ 252/389 A Primary Examiner—Benjamin R. Padgett
Assistant Examiner—Irwin Gluck
Attorney, Agent, or Firm—Luther A. R. Hall

[57] ABSTRACT

A method of treating an aqueous system to inhibit the corrosion of metals in contact therewith and/or inhibit the deposition of scale therefrom comprising adding to the aqueous system a minor proportion of a compound of the formula:

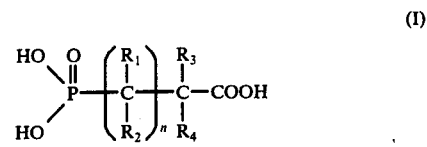

(I)

wherein $n$ is 0 or 1 and when $n$ is 0, $R_3$ and $R_4$ are the same or different and each is hydrogen, an alkyl group having from 1 to 4 carbon atoms, a benzyl, allyl, —CH$_2$PO$_3$H$_2$— or —CHCOOH.CH$_2$COOH group or a group of formula

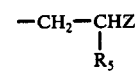

wherein $R_5$ is hydrogen, a methyl, —CH$_2$COOH or —CH$_2$CH$_2$COOH group and Z is a group —COOH or —PO$_3$H$_2$, with the proviso that when Z is a PO$_3$H$_2$ group then $R_5$ is hydrogen or methyl, and when $n$ is 1, $R_1$ and $R_2$ are the same or different and each is hydrogen, or a methyl or phenyl residue and $R_3$ is hydrogen and $R_4$ is hydrogen, an alkyl group having from 1 to 4 carbon atoms or a —CH$_2$CH$_2$COOH group, or $R_3$ and $R_4$ together may form a methylene group =CH$_2$.

14 Claims, No Drawings

CORROSION INHIBITORS

The present invention relates to the use of phosphonocarboxylic acids as corrosion inhibitors and/or scale control agents in aqueous systems.

Traditionally chromates, dichromates, nitrites, benzoates, silicates, polyphosphates etc. have been used to combat corrosion. However, each of these inhibitors suffers from at least one serious disadvantage. Chromates and dichromates are toxic and disposal of them to water courses presents severe ecological problems. Inorganic nitrites require high dose levels to function effectively and they are also subject to bacterial decomposition. This necessitates the use of an expensive organic biocide since chlorine cannot be used as it reacts with nitrite. Benzoates and silicates also require high dose levels and silicates, furthermore, tend to coat metal surfaces with a hydrated silica gel which is often very difficult to remove.

Polyphosphates are effective as relatively low dosage rates but suffer from hydrolysis to phosphate especially at high temperature and at pHs below 7. The phosphate ions liberated on a hydrolysis are not effective as corrosion inhibitors, give rise to sludge problems due to the precipitation of calcium orthophosphate and serve as nutrient for biological growth unless chlorine or another biocide is used.

In an attempt to overcome the problems associated with polyphosphate hydrolysis, corrosion inhibitor systems based on the more hydrolytically stable organic phosphonates have been developed. Examples of acid phosphonates include hydroxy- and amino-diphosphonic acids, e.g. those described in German Patent Specification No. 2,225,645.

According to the present invention, there is provided a method of treating an aqueous system to inhibit the corrosion of metals in contact therewith and/or inhibit the deposition of scale therefrom comprising adding to the aqueous system a minor proportion of a compound of the formula:

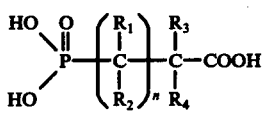

(I)

wherein $n$ is 0 or 1 and when $n$ is 0, $R_3$ and $R_4$ are the same or different and each is hydrogen, an alkyl group having from 1 to 4 carbon atoms, a benzyl, allyl, $-CH_2PO_3H_2-$ or $-CHCOOH \cdot CH_2COOH$ group or a group of formula

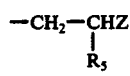

wherein $R_5$ is hydrogen, a methyl, $-CH_2COOH$ or $-CH_2CH_2COOH$ group and Z is a group $-COOH$ or $-PO_3H_2$, with the proviso that when Z is a $PO_3H_2$ group then $R_5$ is hydrogen or methyl, and when $n$ is 1, $R_1$ and $R_2$ are the same or different and each is hydrogen, or a methyl or phenyl residue and $R_3$ is hydrogen and $R_4$ is hydrogen, an alkyl group having from 1 to 4 carbon atoms or a $-CH_2CH_2COOH$ group, or $R_3$ and $R_4$ together may form a methylene group $=CH_2$.

The compounds of formula I may be employed in the method of the invention as the free acids or as water-soluble salts or partial esters.

As examples of water-soluble salts of the compounds of formula I there may be mentioned alkali metal salts e.g. the sodium and potassium salts, ammonium salts, as well as salts of amines e.g. mono-, di- or triethanolamines.

Examples of water-soluble partial esters of the compounds of formula I are those derived from alcohols containing from 1 to 4 carbon atoms.

Preferred compounds of formula I for use according to the invention are those wherein:

$n$ is 0, $R_3$ is hydrogen and $R_4$ has its previous significance $n$ is 1, $R_1$ and $R_3$ are hydrogen and either $R_2$ is hydrogen and $R_4$ is hydrogen, an alkyl group having from 1 to 4 carbon atoms or $-CH_2CH_2COOH$, or $R_2$ is methyl and $R_4$ is hydrogen.

Particularly preferred compounds are those wherein $n$ is 0 and $R_3$ and $R_4$ are each hydrogen or $n$ is 1 and $R_1$, $R_2$ and $R_3$ are hydrogen and $R_4$ is methyl.

Specific examples of corrosion inhibitors of formula I include:

1. 2-phosphonoacetic acid
2. 2-phosphonopropionic acid
3. 2-phosphonohexanoic acid
4. 2-phenyl-2-phosphonopropionic acid
5. 2-phosphonopent-4-enoic acid
6. 2-methyl-2-phosphonopropionic acid
7. 2-butyl-2-phosphonohexanoic acid
8. 2-methyl-2-phosphonohexanoic acid
9. 2-methyl-3-phenyl-2-phosphonopropionic acid
10. 2,3-diphosphonopropionic acid
11. 1-phosphonopropane-1,2,3-tricarboxylic acid
12. 1-phosphonopropane-1,3-dicarboxylic acid
13. 3-methyl-1-phosphonopropane-1,3-dicarboxylic acid
14. 1-phosphonobutane-1,3,4-tricarboxylic acid
15. 1-phosphonopentane-1,3,5-tricarboxylic acid
16. 2,4-diphosphonobutyric acid
17. 2,4-diphosphonopentanoic acid
18. 3-phosphonopentane-1,3,5-tricarboxylic acid
19. 5-phosphonononane-1,3,5,7,9-pentacarboxylic acid
20. 3-phosphonoheptane-1,3-dicarboxylic acid
21. 1-phenyl-2-phosphonobutane-2,4-dicarboxylic acid
22. 3-phosphonopropionic acid
23. 3-phosphonobutanoic acid
24. 2-methyl-3-phosphonobutanoic acid
25. 3-phenyl-3-phosphonopropionic acid
26. 2-methyl-3-phosphonopropionic acid
27. 2-butyl-3-phosphonopropionic acid
28. 1-phosphonobutane-2,4-dicarboxylic acid
29. 2-phosphonomethylacrylic acid In the Examples, the same numbering is used to designate the various compounds under test.

The phosphonic-carboxylic acids of the invention are mostly known compounds and are prepared by hydrolysis of the corresponding esters or nitriles. These phosphorous containing esters or nitriles are prepared by methods well known in the organo-phosphorus literature, namely:

When $n = 1$

A. These compounds may be prepared by base-catalysed addition of a dialkylphosphite to an $\alpha$, $\beta$-unsaturated ester or nitrile (see e.g. Houben-Weyl, Methoden der Organischen Chemie, Band XII/1, pp. 465-74)

When $n = 0$

The intermediate esters

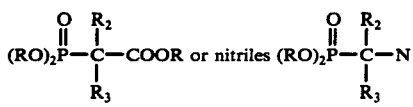

can be prepared in several ways.

B 1. By a Michaelis-Arbuzov reaction between an α-halocarboxylic ester or nitrile and a trialkylphosphite e.g. where $R_2 = R_3 = H$ or $R_2 = H$, $R_3 = Me$ (see e.g. Houben-Weyl, Methoden der Organischen Chemie, Band XII/1, p. 433).

B 2. By alkylation of an intermediate ester

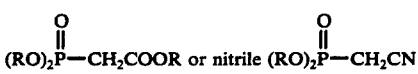

e.g. where $R_2 = H$, $R_3 = Bu$ (see e.g. A.N. Pudovik et al., Zhur.Obshch.Khim, 1957, 27, 2367).

B 3. By base-catalysed addition of an intermediate ester

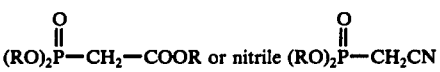

to 1 or 2 moles of an α,β-unsaturated ester or nitrile (see e.g. A.N. Pudovik and N.M.Lebedeva, Zhur.Obshch. Khim. 1955, 25, 1920).

B 4. By a combination of (1) or (2) and (3) above.

The compound

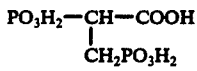

may be prepared as described by B.E. Ivanov et. al., Izv.Akad. Nauk. SSSR,Ser.Khim, 1969, 1851-3

The compound

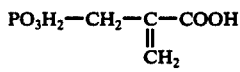

may be prepared as described by B.E. Ivanov et al., Izv.Akad. Nauk SSSR, Ser.Khim, 1970, 96-100

The following compounds of formula I are new and were prepared by the known methods outlined above.

| Compound of formula I | Method of production |
|---|---|
| CH₂CHCOOHCH₂CH₂COOH<br>\|<br>H₂O₃P—CH—COOH | B (3) |
| CH₂CH₂PO₃H₂<br>\|<br>H₂O₃P—CH—COOH | B (3) |
| CH₂Ph<br>\|<br>H₂O₃P—C—COOH<br>\|<br>CH₂CH₂COOH | B (2) and (3) |
| CH₂CH₂PO₃H₂<br>\|<br>H₂O₃P—C—COOH<br>\|<br>CH₂CH₂PO₃H₂ | B (3) |
| CH₂CHCOOHCH₂CH₂COOH<br>\|<br>H₂O₃P—C—COOH<br>\|<br>CH₂CHCOOHCH₂CH₂COOH | B (3) |
| H₂O₃P—CH₂—CH—COOH<br>\|<br>CH₂CH₂COOH | A |

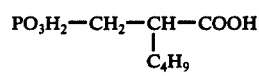

may be prepared by alkylation of intermediate ester

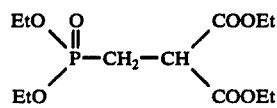

(B.E. Ivanov et al., Izv. Akad. Nauk.SSSR,Ser.-Khim., 1969,889-893) followed by hydrolysis and decarboxylation.

The addition of the compounds of formula I to aqueous systems had been found to inhibit the corrosion of ferrous metals in contact with the aqueous system and/or to inhibit the precipitation of scale-forming salts of calcium, magnesium, barium and strontium from the aqueous systems so treated.

In performing its role as a corrosion inhibitor, the compound of formula I may be used alone or in conjunction with other corrosion inhibitors such as zinc, phosphates, polyphosphates, nitrites e.g. sodium nitrile, sodium chromate, nitrates e.g. sodium nitrate, benzotriazole, bis-benzotriazole or copper-deactivating benzotriazole derivatives, N-acyl sarcozines, triethanolamines, fatty amines, and polycarboxylic acids e.g. polymaleic acid and polyacrylic acid as well as their respective alkali metal salts. The compounds of formula I have been found to be particularly active in inhibiting ferrous metal corrosion when used in conjunction with zinc ions, nitrite ions, phosphate ions, polyphosphate ions and benzotriazoles or derivatives thereof. Normally, the total amount of corrosion inhibitor will be within the range of from 1 to 200 ppm especially from 1 to 100 ppm of the aqueous system.

Combinations of corrosion inhibitors according to the present invention preferably contain from 20 to 97.5%, more preferably from 40 to 90% of the phosphonocarboxylic acid and from 2.5 to 80%, more preferably from 10 to 60% of the other corrosion inhibitor or inhibitors.

In their role as a scale-inhibitor, the compounds of formula I may be used alone or in conjunction with other compounds known to be useful in water treatment.

Dispersing and/or threshold agents may be used, such as for example polymerised acrylic acid and its salts, hydrolysed polyacrylonitrile, polymerised methacrylic acid and its salts, polyacrylamide and co-polymers thereof from acrylic and methacrylic acids, lignin sulphonic acid and its salts, tannin, naphthalene sulphonic acid/formaldehyde condensation products, starch and its derivatives, and cellulose. Specific threshold agents such as for example, hydrolysed polymaleic anhydride and its salts, alkyl phosphonic acids, 1-aminoalkyl, 1,1-diphosphonic acids and their salts and alkali metal phosphates, may also be used.

Precipitating agents such as alkali metal orthophosphates, carbonates and hydroxides, oxygen scavengers such as alkali metal sulphites and hydrazine, sequestering agents such as nitrilotriacetic acid and their salts, ethylene diamine tetraacetic acid and its salts, antifoaming agents such as distearylsebacamide, distearyl adipamide and related products derived from ethylene oxide condensations, in addition to fatty alcohols, such as capryl alcohols and their ethylene oxide condensates may also be used.

In addition to their use in purely aqueous systems, the phosphonocarboxylic acids, alone or in admixture with other corrosion inhibitors, are also useful in systems containing only a proportion of water such as hydraulic fluids and cutting fluids.

The following Examples further illustrate the present invention. Parts and percentages shown therein are by weight unless otherwise stated.

EXAMPLE 1

A mixture of triethylphosphonoacetate (11.2 parts) and diethylvinylphosphonate (8.2 parts) was heated to 40° C and treated with 5 drops of a saturated solution of sodium ethoxide in ethanol. When the exothermic reaction had subsided (maximum temp. 110°) the resulting mixture was heated at 100° for 1 hour, then cooled and dissolved in 100 parts by volume of chloroform. The chloroform solution was washed with water, dried over $MgSO_4$ and distilled to give 7 parts of the pentaethyl ester of 2,4-diphosphonobutyric acid, boiling at 184°-190°/4mm.

Hydrolysis of this material by heating at reflux in 75 parts by volume of 18% hydrochloric acid gave, after evaporation, 2,4-diphosphonobutyric acid hydrate as a highly viscous oil, having the following elemental analysis by weight:

Calculated for $C_4H_{10}O_8P_2.H_2O$: C, 18.04%; H, 4.51%; P, 22.30%. Found: C, 17.84%; H, 4.43%; P, 22.73%.

EXAMPLE 2

A mixture of diethylvinyl phosphonate (16.4 parts) and diethylphosphonoacetonitrile (8.9 parts) was heated to 40° and treated with 10 drops of a saturated solution of sodium ethoxide in ethanol. The resulting solution was heated at 100° for 1 hour, cooled and dissolved in 100 parts by volume of chloroform. The chloroform solution was washed with water, dried over $MgSO_4$ and the chloroform removed by evaporation to give a viscous residual oil (17 parts) comprising mainly of 3-cyano-1,3,5-tris(diethylphosphono) pentane.

Hydrolysis of this material in 100 parts by volume of refluxing 18% hydrochloric acid, followed by evaporation, redissolution in water and elution down an anion exchange column, and final evaporation to dryness, gave a hygroscopic sample of 1,3,5-triphosphonopentane-3-carboxylic acid, having the following elemental analysis by weight:

Calculated for $C_6H_{15}O_{11}P_3.H_2O$: C, 19.25%; H, 4.54%; P, 24.87%. Found: C, 19.08%; H, 4.87%; P, 23.64%.

EXAMPLE 3

A mixture of 2,4-dicyanobut-1-ene (21.2 parts) and triethylphosphonoacetate (44 parts) was treated with 10 drops of a saturated solution of sodium ethoxide in ethanol and heated at 100° for 4 hours. The reaction solution was dissolved in chloroform (100 parts by volume) washed with water, dried over $MgSO_4$ and distilled to give 19 parts of ethyl (2-diethylphosphono-4,6-dicyano)-hexanote boiling at 206°-208°/0.1mm.

This material was heated to reflux for 18 hours in 150 parts by volume of 18% hydrochloric acid. After evaporation the residue was treated with 200 parts by volume of acetone and the insoluble $NH_4Cl$ removed by filtration. Evaporation of the acetone gave 1-phosphonopentane-1,3,5-tricarboxylic acid (monohydrate) as a highly viscous oil having the following elemental analysis by weight:

Calculated for $C_8H_{13}O_9P.H_2O$: C, 31.80%; H, 4.97%; P, 10.27%. Found: C, 32.23%; H, 5.25%; P, 10.43%.

EXAMPLE 4

A mixture of 2,4-dicyanobut-1-ene (21.2 parts) and diethylphosphonoacetonitrile was (17.7 parts) treated with 10 drops of saturated sodium ethoxide in ethanol as in Example 3 (above) to give an undistillable 2:1 adduct. This was hydrolysed and isolated as in Example 3 to give a crude sample of 5-phosphononane-1, 3,5,7,9-pentacarboxylic acid, whose nuclear magnetic resonance spectrum ($^1H, ^{31}P$) was consistent with the proposed structure.

EXAMPLE 5

A mixture of 2,4-dicyanobut-1-ene (21.2 parts) and diethylphosphite (27.6 parts) was heated to 70° and treated dropwise with a saturated solution of sodium ethoxide in ethanol until the exothermic reaction ceased. The reaction mass was cooled, treated with 2 parts by volume of acetic acid and distilled to give 29 parts of 1-diethylphosphono-2,4-dicyanobutane, boiling at 183°-4°/0.2mm and having the following elemental analysis by weight:

Calculated for $C_{10}H_{17}N_2O_3P$: C, 49.20%; H, 7.02%; P, 11.48%. Found: C, 49.14%; H, 6.98%; P, 11.67%.

This material was hydrolysed and worked up as in Example 3 to give 1-phosphonobutane-2,4-dicarboxylic acid as a hydrate having the following elemental analysis by weight:

Calculated for $C_6H_{11}O_7P.1.5\ H_2O$: C, 28.65%; H, 5.58%; P, 12.34%. Found: C, 28.73%; H, 5.20%; P, 12.35%.

EXAMPLE 6

Diethyl diethylphosphonomethylmalonate (31 parts) was added dropwise to a stirred solution of sodium (2.3 parts) in ethanol (250 parts by volume). After 15 mins the solution was treated n-butylbromide (15.3 parts). The mixture was stirred at 25° for 30 mins and heated to reflux for a further 2 hours. After removal of the ethanol by evaporation the residual oil was taken up in chloroform (200 parts by volume), washed with water, dried over $MgSO_4$ and distilled to give diethyl diethylphosphomomethylbutylmalonate (7.9 parts) boiling at 128°-130°/0.1mm.

Hydrolysis of this material in refluxing 18% hydrochloric acid (100 parts by volume) gave after evaporation 3,4 parts of 2-phosphonomethylhexanoic acid hydrate, as a viscous oil having the following elemental analysis by weight:

Calculated for $C_7H_{15}O_5P \cdot H_2O$: C, 36.84%; H, 7.46%; P, 13.60%. Found: C, 35.50%; H, 6.93%; P, 13.90%.

The nuclear magnetic resonance spectrum ($^1H, ^{31}P$) was consistent with the proposed structure.

EXAMPLES 7 to 38

Evaluation of Corrosion Inhibition by the Aerated Solution Bottle Test

To carry out the Aerated Solution Bottle Test, a standard corrosive water is made up from:

20 g. $CaSO_4 \cdot 2H_2O$
15 g. $MgSO_4 \cdot 7H_2O$
4.6 g. $NaHCO_3$
7.7 g. $CaCl_2 \cdot 6H_2O$
45 gallons Distilled water Mild steel coupons, 5 cms. × 2.5 cms are scrubbed with pumice, immersed for one minute in hydrochloric acid and then rinsed, dried and weighed.

The desired proportion of additive combination is dissolved in 100 ml. of standard corrosive water. A steel coupon is suspended in the solution, and the whole is stored in a bottle in a thermostat at 40° C. During the storage period, air is passed into the solution at 500 ml/minute, the passage of the air being screened from the steel coupon; any water losses by evaporation are replaced as they occur with distilled water from a constant head apparatus.

After 48 hours, the steel coupon is removed, scrubbed with pumice, immersed for one minute in hydrochloric acid inhibited with 1% by weight of hexamine and then rinsed, dried and reweighed. A certain loss in weight will have occured.

A blank test i.e. immersion of a mild steel specimen in the test water in the absence of any potential corrosion inhibitor, is carried out with each series of tests. The corrosion rates are calculated in milligrams of weight loss/sq. decimeter/day (m.d.d.) but for convenience the results are shown as percentage protection, which is defined as follows:

$$\% \text{ Protection} = \frac{\text{Corrosion rate for blank (in mdd)} - \text{corrosion rate for sample (in mdd)}}{\text{Corrosion rate for blank (in mdd)}} \times 100$$

The results obtained using individual corrosion inhibitors according to the invention are given in Table I.

TABLE I
Aerated Solution Bottle Test for individual corrosion inhibitors of formula I

| Example | Corrosion Inhibitor under test | % Protection |
|---|---|---|
| 7 | Compound No. 11 | 72 |
| 8 | Compound No. 10 | 98 |
| 10 | Compound No. 26 | 94 |
| 11 | Compound No. 23 | 83 |
| 12 | Compound No. 3 | 80 |

The results obtained in the Aerated Solution Bottle Test using mixtures of corrosion inhibitors consisting of a compound of formula I with zinc, nitrite and phosphate ions are shown in Table 2.

Table 2
Aerated Solution Bottle Test results using corrosion inhibitors of formula I with zinc, nitrite and phosphate ions.

| Example | Compound | Blank corrosion Rate (mdd) | % Protection 50 ppm compound +50 ppm $Zn^{++}$ | % Protection 50 ppm compound +50 ppm $NO_2$ | % Protection 50 ppm compound +50 ppm $HPO_4^{2-}$ |
|---|---|---|---|---|---|
| 13 | 1 | 93 | 92 | 85 | 86 |
| 14 | 2 | 78 | 49 | — | 89 |
| 15 | 3 | 83 | 92 | 95 | 84 |
| 16 | 4 | 63 | 92 | 84 | 83 |
| 17 | 10 | 92 | 87 | 68 | 91 |
| 18 | 11 | 115 | 83 | 61 | 15 |
| 19 | 15 | 83 | 100 | 90 | 95 |
| 20 | 16 | 70 | 79 | 93 | 79 |
| 21 | 18 | 100 | 99 | 29 | 0 |
| 22 | 19 | 109 | 89 | 87 | 42 |
| 23 | 21 | 73 | 99 | 97 | 82 |
| 24 | 22 | 92 | 100 | 99 | 30 |
| 25 | 23 | 94 | 94 | — | 34 |
| 26 | 25 | 63 | 84 | 0 | 46 |
| 27 | 26 | 83 | 96 | 96 | 25 |
| 28 | 27 | 82 | 98 | — | 12 |
| 29 | 28 | 73 | 100 | 100 | 84 |
| 30 | 29 | 103 | 95 | 93 | 83 |

The results obtained, using various combinations of corrosion inhibitors according to the invention, are set out below in Table 3.

Table 3
Aerated Solution Bottle Test Results for various combinations of corrosion inhibitors of formula I with zinc, phosphate, nitrite or polyphosphate ions.

| Example | Compound 1 (ppm) | Zinc (ppm) | % Protection |
|---|---|---|---|
| 31 | 100 | 0 | 87 |
|  | 80 | 20 | 97 |
|  | 60 | 40 | 94 |
|  | 40 | 60 | 91 |

Table 3-continued

Aerated Solution Bottle Test Results for various combinations of corrosion inhibitors of formula I with zinc, phosphate, nitrite or polyphosphate ions.

| | 20 | 80 | 52 |
|---|---|---|---|
| | 0 | 100 | 0 |
| | Blank corrosion rate | 88 mdd | |

| Example | Compound 1 (ppm) | Phosphate (ppm) | % Protection |
|---|---|---|---|
| 32 | 100 | 0 | 88 |
| | 80 | 20 | 93 |
| | 60 | 40 | 90 |
| | 40 | 60 | 70 |
| | 20 | 80 | 69 |
| | 0 | 100 | 24 |
| | Blank corrosion rate | 120 mdd | |

| Example | Compound 3 (ppm) | Zinc (ppm) | % Protection |
|---|---|---|---|
| 33 | 100 | 0 | 98 |
| | 80 | 20 | 90 |
| | 60 | 40 | 92 |
| | 40 | 60 | 96 |
| | 20 | 80 | 64 |
| | 0 | 100 | 0 |
| | Blank corrosion rate | 73 mdd | |

| Example | Compound 3 (ppm) | Nitrite (ppm) | % Protection |
|---|---|---|---|
| 34 | 100 | 0 | 87 |
| | 80 | 20 | 93 |
| | 60 | 40 | 94 |
| | 40 | 60 | 100 |
| | 2 | 80 | 93 |
| | 0 | 100 | 0 |
| | Blank corrosion rate | 109 mdd | |

| Example | Compound 10 (ppm) | Phosphate (ppm) | % Protection |
|---|---|---|---|
| 35 | 50 | 0 | 61 |
| | 40 | 10 | 54 |
| | 30 | 20 | 95 |
| | 20 | 30 | 85 |
| | 10 | 40 | 74 |
| | 0 | 50 | 26 |
| | Blank corrosion rate | 97 mdd | |

| Example | Compound 28 (ppm) | Zinc (ppm) | % Protection |
|---|---|---|---|
| 36 | 100 | 0 | 19 |
| | 80 | 20 | 100 |
| | 60 | 40 | 97 |
| | 40 | 60 | 99 |
| | 20 | 80 | 3 |
| | 0 | 100 | 0 |
| | Blank corrosion rate | 73 mdd | |

| Example | Compound 28 (ppm) | Nitrite (ppm) | % Protection |
|---|---|---|---|
| 37 | 100 | 0 | 19 |
| | 80 | 20 | 94 |
| | 60 | 40 | 79 |
| | 40 | 60 | 91 |
| | 20 | 80 | 94 |
| | 0 | 100 | 21 |
| | Blank corrosion rate | 109 mdd | |

| Example | Compound 29 (ppm) | Polyphosphate (ppm) | % Protection |
|---|---|---|---|
| 38 | 50 | 0 | 41 |
| | 40 | 10 | 76 |
| | 30 | 20 | 72 |
| | 20 | 30 | 61 |
| | 10 | 40 | 41 |
| | 0 | 50 | 0 |
| | Blank corrosion rate | 64 mdd | |

EXAMPLES 39 to 43

Evaluation of Corrosion Inhibition by the Laboratory Heat Exchanger Rig Test

Some laboratory tests were carried out using a Laboratory Heat Exchanger Rig, a form of laboratory testing intended to similate practical use conditions more closely than does the Aerated Solution Bottle Test described in Examples 1–27.

In this rig, corrosive water is aerated and circulated over a number of metal coupons, and is heated by being passed through a heated steel heat exchanger tube. After a suitable test period, the metal coupons and the heat exchanger tube are examined, and their state assessed.

In detail, the rig consists of a closed water circuit, made up of the following items in order,
20 liter reservoir
1 liter reservoir
flow meter
coupon chamber
heat exchanger
cooling condenser Corrosive water in the 20 liter reservoir is aerated with compressed air introduced through a sintered disc at about 5 liters per minute, and is then pumped to the 1 liter reservoir. From this reservoir it is pumped through the flow meter to the glass coupon chamber in which are a number of rectangular metal coupons each 2.5 by 5.0 cms. mounted on a perspex jig. The water then flows through the heat exchanger which is made up of a ⅜ inch internal diameter steel tube with copper end pieces around which is wound a 960 watt heater coil; from the heat exchanger the water flows through the cooling condenser back to the 20 liter reservoir.

A flow rate in the circuit of about 1.0 gallon per minute provides a velocity of about 1.5 feet per second and a Reynolds number of 8500 in the heat exchanger. The heater coil gives the heat exchanger tube a skin temperature of about 60° C. and the water leaves at about 45° C., a difference across the heat transfer surface of some 15° C. The cooling condenser is so operated as to cool the water to about 40° C. before it begins a fresh circuit.

Metal coupons are scrubbed with pumice and then immersed in acid as follows:

| metal | acid |
|---|---|
| mild steel | Conc. HCl diluted 1:1 with water at room temperature for 1 minutes |
| copper | " |
| brass | " |
| aluminum | 5% phosphoric acid/2% chromic acid, at 75° C. for 5 minutes |

After such immersion, the coupons are rinsed with water, dried and weighed; they are then mounted on a perspex jig, care being taken to ensure that none of the coupons touch each other, and that they are insulated from the bolt holding the jig together. The heat exchanger tube is cleaned with pumice dipped in conc. hydrochloric acid diluted 1:1 with water, and then rinsed in water and dried.

The rig is assembled, and cleaned thoroughly by circulating conc. hydrochloric acid diluted 1:1 with water, then flushing with tap water for about half an hour (about 30 gallons in all) and draining. The necessary quantity of additives to produce the desired concentrations is put into one of the reservoirs and the rig is filled with 22 litres of a standardised corrosive test water, which is characterised as follows:

| | | |
|---|---|---|
| Phenol Alkalinity | : 0 | |
| Total Alkalinity | : 20 | |
| Temp. Hardness | : 20 | as p.p.m. of $CaCO_3$ |
| Perm. Hardness | : 0 | |
| Total Hardness | : 20 | |
| Chloride | : 15 | p.p.m. |
| Total Dissolved Solids | : 70 | p.p.m. |

The pump is primed and started, and the heater switched on.

The concentration of inhibitor and the water level in the rig are checked daily.

After approximately ten days, the heat exchanger tube is removed, sectioned and examined. The test coupons are removed and the mild steel, brass and copper coupons are cleaned as before except that the acid is inhibited with 1% hexamine, rinsed, dried and re-weighed. The aluminium specimens are scrubbed, dried and re-weighed.

The results observed enable an assessment to be made of the anti-corrosive action of the inhibitor under test.

Using this test procedure the following results were obtained as shown in Table 4, following.

Table 4
Laboratory Heat Exchanger Rig Tests

| Ex. | Initial level of corrosion inhibitor | | Length of Test (Days) | Corrosion Rates (mdd) | | | | | |
|---|---|---|---|---|---|---|---|---|---|
| | | | | Mild steel | Cast iron | Aluminium | Solder | Copper | Brass |
| — | None | | 17 | 142.5 | 89.1 | 2.0 | 5.0 | 1.9 | 1.6 |
| 39 | Compound 1 + Zinc + Benzotriazole | 40ppm 10ppm 2ppm | 13 | 2.7 | 7.2 | 1.2 | 3.2 | 0 | 0.1 |
| 40 | Compound 1 + Zinc + Polyphosphate + Benzotriazole | 30ppm 10ppm 10ppm 2ppm | 8 | 15.9 | 52.0 | 1.1 | 5.5 | 1.2 | 1.5 |
| 41 | Compound 26 + Zinc + Benzotriazole | 40ppm 10ppm 2ppm | 13 | 5.0 | 46.2 | 0.9 | 3.5 | 0.1 | 0.1 |
| 42 | Compound 28 + Zinc + Benzotriazole | 75ppm 25ppm 2ppm | 10 | 24.4 | 37.7 | 1.5 | 4.4 | 0 | 0.3 |
| 43 | Compound 29 + Zinc + Polyphosphate + Benzotriazole | 24ppm 24ppm 10ppm 2ppm | 11 | 2.6 | 1.4 | 0.1 | 0 | 0.2 | 0.2 |

EXAMPLES 44 AND 45

Evaluation of Anti-Scaling Activity

A mild steel heater sheath into which was inserted a 1 KW Firerod cartridge heater was immersed in a solution containing $Mg^{2+}$ ions and $HCO_3^-$ ions. 2 Liters of a solution containing 6.5 g/l. $Mg(NO_3)_2.6H_2O$ and 2 liters of a solution containing 4.0 g/l. $NaHCO_3$ were prepared. The additive to be evaluated was added to the magnesium nitrate solution, the additive concentration being calculated on the total 4 liters of solution. 1 Liter of each solution was mixed in a beaker and the heater sheath immersed in the solution. As the solution evaporated the remaining 2 liters of mixed solutions were added at such a rate that a constant volume of 2 liters was maintained in the test solution. After 5 hrs., 2 liters of the solution had evaporated, giving a concentration factor of 2. The heater sheath was removed from the solution and allowed to dry. The weight of scale formed on the sheath was recorded and the thickness of the scale deposit around the central part of the sheath measured using an Elcometer. The magnesium content of the final solution was determined by titration.

The results obtained using two individual compounds of formula I in this test are set out in Table 5. When the test is operated in the absence of additive the final solution is cloudy due to precipitated magnesium hydroxide, hence the result shown in Table 5 for the blank is not a true indication of the result.

Table 5

High Temperature Scale Test Results

| Ex. | Compound | Conc. ppm. | Wt. of Scale gm. | Scale Thickness thou. | ppm $M_g^{2+}$ in final solution | Type of Scale |
|---|---|---|---|---|---|---|
| 44 | Compound No. 16 | 10 | 0.725 | 3–5 | 357.3 | V. hard non-uniform |
| 45 | Compound No. 11 | 10 | 0.64 | 4–5 | 345.3 | V. hard non-uniform |
| — | Control | — | 2.1 | 20 | 150 | — |

EXAMPLES 46 TO 49

Evaluation of Corrosion Inhibition in Aqueous Hydraulic Systems

The following method is a modification of the Institute of Petroleum's Test Method IP 287/74.

1.0%, 0.5% and 0.25% weight/volume solutions of various compounds of formula I were prepared in deionised water and neutralized to pH 8.0 with triethanolamine.

Cast iron chips were prepared, sieved, washed and dried in accordance with the IP 287 procedure and placed on a filter paper contained in a petri dish in order to cover a 35 mm square. 2 ml. of the solution under test were pipetted over the chips to wet them uniformly and the dish was covered with a lid. After two hours the chips were washed from the filter paper which was then dried with warm air. If corrosion of the cast iron chips occurs, brown spots develop on the filter paper to an extent which is dependent upon the degree of corrosion. A visual assessment of the total area of these spots is made with the aid of a graticule and the result is expressed as a percentage of the total surface area. Diffuse staining is ignored.

The results obtained are set out in the following Table 6.

Table 6

Modified IPTM 287/74 Results

| Ex. | Compound of formula I | Concentration of Compound I (%) | Area covered by rust (%) |
|---|---|---|---|
| — | — | — | 40 |
| 46 | Compound No. 1 | 1.00 | 0 |
|  |  | 0.50 | 0 |
|  |  | 0.25 | 10 |
| 47 | Compound No. 12 | 1.00 | 0 |
|  |  | 0.50 | 0 |
|  |  | 0.25 | 10 |
| 48 | Compound No. 29 | 1.00 | 3 |
|  |  | 0.50 | 5 |
|  |  | 0.25 | 15 |
| 49 | Compound No. 26 | 1.00 | 0–1 |
|  |  | 0.50 | 5 |
|  |  | 0.25 | 15 |

What we claim is:

1. A method of treating an aqueous system to inhibit the corrosion of metals in contact therewith and to inhibit the deposition of scale therefrom which comprises
adding to the aqueous system a minor proportion of a compound of the formula

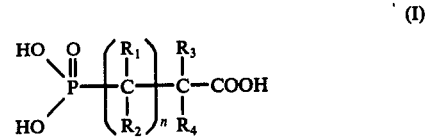

wherein $n$ is 0 or 1, and when $n$ is 0, $R_3$ and $R_4$ are each hydrogen; or when $n$ is 1, $R_1$, $R_2$, $R_3$ and $R_4$ are each hydrogen; or when $n$ is 1, $R_1$, $R_2$ and $R_3$ are hydrogen, and $R_4$ is methyl.

2. A method as claimed in claim 1 wherein the water-soluble salt of the compound of formula I is an alkali metal salt, an ammonium salt or an amine salt.

3. A method as claimed in claim 1 wherein the water-soluble partial ester of the compound of formula I is derived from an alcohol having from 1 to 4 carbon atoms.

4. A method as claimed in claim 1 wherein $n$ is 0 and $R_3$ and $R_4$ are each hydrogen.

5. A method as claimed in claim 1 wherein the compound of formula I is used in conjunction with other corrosion inhibitors.

6. A method as claimed in claim 5 wherein the other corrosion inhibitors are zinc, phosphates, polyphosphates, nitrites, sodium chromate, nitrates, benzotriazole, bis-benzotriazole or copper-deactivating benzotriazole derivatives, N-acyl sarcosines, triethanolamines, fatty amines or polycarboxylic acids.

7. A method as claimed in claim 6 wherein the other corrosion inhibitors are zinc ions, nitrite ions, phosphate or polyphosphate ions or benzotriazoles or derivatives thereof.

8. A method as claimed in claim 7 wherein the corrosion inhibitor of formula I is such that $n$ is 0 and $R_3$ and $R_4$ are each hydrogen and the other corrosion inhibitors are zinc and benzotriazole.

9. A method as claimed in claim 7, wherein the corrosion inhibitor of formula I is such that $n$ is 1 and $R_1$, $R_2$, $R_3$ and $R_4$ are each hydrogen and the other corrosion inhibitors are zinc and benzotriazole.

10. A method as claimed in claim 7 wherein the corrosion inhibitor of formula I is such that $n$ is 1, $R_1$, $R_2$ and $R_3$ hydrogen and $R_4$ is methyl and the other corrosion inhibitors are zinc and benzotriazole.

11. A method as claimed in claim 1 wherein the total amount of corrosion inhibitor is within the range of from 1 to 200 ppm.

12. A method as claimed in claim 11 wherein the total amount of corrosion inhibitor is within the range of from 1 to 100 ppm.

13. A method as claimed in claim 5 wherein the corrosion inhibitor mixture contains 20 to 97.5% of the compound of formula I and 2.5 to 80% of the other corrosion inhibitor or inhibitors.

14. A method as claimed in claim 13 wherein the corrosion inhibitor mixture contains 40 to 90% of the compound of formula I and from 10 to 60% of the other corrosion inhibitor or inhibitors.

* * * * *